United States Patent
Ikits et al.

(10) Patent No.: US 8,442,806 B2
(45) Date of Patent: May 14, 2013

(54) SYSTEMS AND METHODS FOR SIMULATIONS UTILIZING A VIRTUAL COUPLING

(75) Inventors: Milan Ikits, Sunnyvale, CA (US); Donald Douglas Nelson, Montgomery Village, MD (US)

(73) Assignee: Immersion Medical, Inc., Baltimore, MD (US)

( * ) Notice: Subject to any disclaimer, the term of this patent is extended or adjusted under 35 U.S.C. 154(b) by 413 days.

(21) Appl. No.: 12/716,903

(22) Filed: Mar. 3, 2010

(65) Prior Publication Data

US 2011/0218774 A1    Sep. 8, 2011

(51) Int. Cl.
*G06F 17/50* (2006.01)
(52) U.S. Cl.
USPC ...... 703/2; 703/6; 703/21; 715/764; 345/419; 345/420; 434/262
(58) Field of Classification Search ............... 703/2, 21, 703/6; 345/419, 420; 715/764; 434/262
See application file for complete search history.

(56) References Cited

U.S. PATENT DOCUMENTS

| | | |
|---|---|---|
| 4,961,138 A | 10/1990 | Gorniak |
| 5,088,046 A | 2/1992 | McMurtry |
| 5,181,181 A | 1/1993 | Glynn |
| 5,273,038 A | 12/1993 | Beavin |
| 5,296,846 A | 3/1994 | Ledley |
| 5,482,472 A | 1/1996 | Garoni et al. |
| 5,546,943 A | 8/1996 | Gould |
| 5,609,485 A | 3/1997 | Bergman et al. |
| 5,623,582 A | 4/1997 | Rosenberg |
| 5,724,264 A | 3/1998 | Rosenberg et al. |
| 5,769,640 A | 6/1998 | Jacobus et al. |
| 5,821,920 A | 10/1998 | Rosenberg et al. |

(Continued)

FOREIGN PATENT DOCUMENTS

| | | |
|---|---|---|
| DE | 10258952 | 8/2004 |
| JP | H04-332544 | 11/1992 |

(Continued)

OTHER PUBLICATIONS

Baraff, D. et al., Large Steps in Cloth Simulation, Computer graphics Proceedings, Annual Conference Series, 1998, SIGGRAPH 98, Orlando, pp. 43-54.

(Continued)

*Primary Examiner* — Thai Phan
(74) *Attorney, Agent, or Firm* — Kilpatrick Townsend & Stockton LLP

(57) ABSTRACT

Embodiments include storing values of a first plurality of nodes in memory based on tracking the position of a plurality of points of a physical object and maintaining a second plurality of nodes in memory, each node of the second plurality of nodes corresponding to a node of the first plurality. The values of the second plurality of nodes can be used to model interactions with other objects and to render a view of a simulated object. The simulation can access data identifying a simulation boundary and selectively update values of the second plurality of nodes using the first plurality of nodes while ensuring that the simulation boundary is not violated. A value of the second plurality of nodes can be set to be different from the value of the corresponding one of the first plurality of nodes if using the first node's value would violate the boundary.

19 Claims, 8 Drawing Sheets

U.S. PATENT DOCUMENTS

| | | | |
|---|---|---|---|
| 5,882,206 | A | 3/1999 | Gillio |
| 5,956,040 | A | 9/1999 | Asano et al. |
| 5,971,767 | A | 10/1999 | Kaufman et al. |
| 6,193,519 | B1 | 2/2001 | Eggert et al. |
| 6,210,168 | B1 | 4/2001 | Aiget et al. |
| 6,623,433 | B2 | 9/2003 | Webler et al. |
| 6,726,638 | B2 | 4/2004 | Ombrellaro |
| 6,758,676 | B2 | 7/2004 | Eggert et al. |
| 6,929,481 | B1 | 8/2005 | Alexander et al. |
| 6,965,370 | B2 | 11/2005 | Gregoria |
| 7,056,123 | B2 | 6/2006 | Gregorio et al. |
| 7,084,884 | B1 | 8/2006 | Nelson et al. |
| 7,520,749 | B2 | 4/2009 | Ohlsson |
| 7,835,892 | B2 | 11/2010 | Butsev et al. |
| 7,864,173 | B2 * | 1/2011 | Handley et al. ............... 345/420 |
| 2002/0168618 | A1 | 11/2002 | Anderson et al. |
| 2004/0009459 | A1 | 1/2004 | Anderson et al. |
| 2005/0062738 | A1 * | 3/2005 | Handley et al. ............... 345/419 |
| 2005/0271302 | A1 | 12/2005 | Khamene et al. |
| 2006/0064007 | A1 | 3/2006 | Comaniciu et al. |
| 2008/0020362 | A1 | 1/2008 | Cotin et al. |
| 2008/0088578 | A1 | 4/2008 | Ikits et al. |
| 2009/0012755 | A1 | 1/2009 | Nelson et al. |
| 2009/0046140 | A1 * | 2/2009 | Lashmet et al. ................ 348/51 |
| 2011/0014596 | A1 * | 1/2011 | Kurenov et al. .............. 434/262 |
| 2011/0202856 | A1 * | 8/2011 | Handley et al. ............... 715/764 |

FOREIGN PATENT DOCUMENTS

| | | |
|---|---|---|
| JP | H07-171154 | 7/1995 |
| JP | 2002-336247 | 11/2002 |
| JP | 2003-061956 | 3/2003 |
| JP | 2003-067784 | 3/2003 |
| JP | 2003-319939 | 11/2003 |
| JP | 2004-070669 | 3/2004 |
| JP | 2004-070670 | 3/2004 |
| JP | 2004-159781 | 6/2004 |
| JP | 2004-171251 | 6/2004 |
| WO | WO 99/38141 | 7/1999 |
| WO | WO 02/094080 | 11/2002 |
| WO | WO 2004/051602 | 6/2004 |

OTHER PUBLICATIONS

Boxerman, E. et al., Decomposing Cloth, Eurographics/ACM SIGGRAPH Symposium on Computer Animation, 2004, 9 pgs.

Brown, J. et al., Real Time Simulation of Deformable Objects: Tools and Application, Computer Animation, The Fourteenth Conference on Computer Animation Proceedings Nov. 7-8, 2001, pp. 228-236.

Cotin, S., et al., New Approach to Catheter navigation for Interventional Radiology Simulation, MICCAI 2005, Springer Berlin/Heidelberg, LNCS 3750, pp. 534-542.

Cotin, S., et al., A Hybrid Elastic Model for Real-Time Cutting, Deformations, and Force Feedback for Surgery Training and Simulation, The Visual Computer, 2000, vol. 16, pp. 437-452.

Coltin, S. et al., Real Time Elastic Deformations of Soft Tissue for Surgery Simulation, TVCG 1998.

Gregoire, M. et al., Interactive Simulation of One Dimensional Flexible Parts, Association for Computing Machinery Inc., 2006, Cardiff, Wales, United Kingdom, pp. 95-103.

Lenoir, J. et al., Interactive Physically Based Simulation of Catheter and Guidewire, Computer and Graphics, 2006, vol. 30, pp. 416-422.

Lindblad, A. et al., Real Time Finite Element based Virtual Tissue Cutting, MMVR, 2006.

Paolo Baerlocher, Inverse Kinematics Techniques for the Interactive Posture Control of Articulated Figures, 2001, Wcole Polytechnique Federale de Lausanne, XP002506493.

International Search Report and Written Opinion for PCT Application PCT/US2008/063488 dated Dec. 2, 2008.

United States Patent and Trademark Office, Office Action, U.S. Appl. No. 11/774,223 mailed Oct. 5, 2009.

United States Patent and Trademark Office, Office Action, U.S. Appl. No. 11/774,223 mailed Aug. 26, 2010.

Bates, Lisa M. et al., "A Method for Ultrasound Image Based Correction of Intraoperative Brain Shift," Proc. SPIE Medical Imaging 2000; Image Display and Visualization 3976: pp. 58-68.

Bro-Nielsen, Morten, "Finite Element Modeling in Surgery Simulation," Proceedings of The IEEE, vol. 86, No. 3, Mar. 1998, pp. 490-503.

Chen, Hongsheng et al., "Fast Voxelization of Three-Dimensional Synthetic Objects," Journal of Graphics Tools, vol. 3, No. 4, 1998, pp. 33-45.

Freidlin Raisa Z. et al., "NIHmagic: 3D Visualization, Registration and Segmentation Tool," 28th AIPR Workshop: 3D Visualization for Data Exploration and Decision Making, Proc. of SPIE vol. 3905, 2000, pp. 8 pages.

Hesina, Gerd et al., "Distributed Open Inventor: A Practical Approach to Distributed 3D Graphics," Vienna University of Technology, Austria, 1999, pp. 74-81.

Iwata, Hiroo et al., "Volume Haptization", Institute of Engineering Mechanics, 1993, pp. 16-23.

Kreeger, Kevin et al., "Mixing Translucent Polygons with Volumes," Dept. of Computer Science, SUNY at Stony Brook, 1999, pp. 191-199.

Minsky, Margaret et al., "Feeling and Seeing: Issues in Force Display," Dept. of Computer Science, 1990, pp. 235-242, 270.

Stanley, Michael C. et al., "Computer Simulation of Interacting Dynamic Mechanical Systems Using Distributed Memory Parallel Processors," DSC—vol. 42, Advances in Robotics, ASME 1992, pp. 55-61.

Su, S. Augustine et al., "The Virtual Panel Architecture: A 3D Gesture Framework," Computer Science Department, 1993, pp. 387-393.

Weiler, Manfred et al., "Direct Volume Rendering in OpenSG," Computers & Graphics 28,2004, pp. 93-98.

Weiskopf, Daniel et al., "Volume Clipping via Per-Fragment Operations in Texture-Based Volume Visualization," Visualization and Interactive Systems Group, 2002, pp. 93-100.

Westermann, Rudiger et al., "Efficiently Using Graphics Hardware in Volume Rendering Applications," Computer Graphics Proceedings, Annual Conference Series, 1998, pp. 169-177.

Yamakita, M. et al., "Tele Virtual Reality of Dynamic Mechanical Model," Proceedings of the 1992 IEEE/RSJ International Conference on Intelligent Robots and Systems, Jul. 7-10, 1992, pp. 1103-1110.

Aiger et al., "Real-Time Ultrasound Imaging Simulation," 1998, 24 pages.

Cotin et al. "Real-Time Elastic Deformations of Soft Tissues for Surgery Simulation", IEEE Transactions of Visualization and Computer Graphics, vol. 5, No. 1, Jan.-Mar. 1999, pp. 62-73.

Ehricke, Hans-Heino, "SONOSim3D: A Multimedia System for Sonography Simulation and Education with an Extensible Case Database", European Journal of Ultrasound 7, 1998, pp. 225-230.

International Preliminary Report on Patentability, International Application No. PCT/US2005/031391, dated Apr. 3, 2007.

Japanese Patent Office, Notice for Reasons of Rejection, Application No. 2007-533500, dated May 11, 2010.

Maul et al. "Ultrasound Simulators: Experience with the SonoTrainer and Comparative Review of Other Training Systems", Ultrasound Obstet Gynecol, Aug. 4, 2004, pp. 581-585.

Office Action by UK Intellectual Property Office, Application No. GB0706763, dated Jul. 1, 2010.

Written Opinion of the International Searching Authority, Application No. PCT/US2005/031391, dated Mar. 1, 2006.

United States Patent and Trademark Office, Office Action, U.S. Appl. No. 10/950,766 mailed Dec. 28, 2007.

United States Patent and Trademark Office, Office Action, U.S. Appl. No. 10/950,766 mailed Jun. 28, 2007.

United States Patent and Trademark Office, Office Action, U.S. Appl. No. 10/950,766 mailed Aug. 11, 2008.

United States Patent and Trademark Office, Office Action, U.S. Appl. No. 10/950,766 mailed Feb. 2, 2009.

United States Patent and Trademark Office, Office Action, U.S. Appl. No. 10/950,766 mailed Jul. 13, 2009.

United States Patent and Trademark Office, Office Action, U.S. Appl. No. 12/946,551 mailed Jan. 24, 2012.

United States Patent and Trademark Office, Office Action, U.S. Appl. No. 12/946,551 mailed Jul. 18, 2011.

Barbic, J. et al., Real-Time Reduced Large-Deformation Models and Distributed Contact for Computer Graphics and Haptics, PhD Thesis, Computer Science Department, School of Computer Science—Carnegie Mellon University, Aug. 2007.

Bhat, S. et al., 3D Real-Time FEM Based Guide Wire Simulator with Force Feedback, Molecular Meets Virtual Reality, James D. Westwood et al (Eds.), IOS Press 2005.

Choi, K. et al., Stable but Responsive Cloth, ACM Transactions on Graphocs, 21(3):604-611, SIGGRAPH 2002.

Golub et al., Matrix Computations, Johns Hopkins University Press, p. 156, 1996.

Muller, M. et al., Interactive Virtual Materials, Graphics Interface, 8 pgs., 2004.

Ortega, M. et al., A Six Degree-of-Freedom God-Object Method for Haptic Display of Rigid Bodies with Surface Properties, IEEE Transactions on Visualization and Computer Graphics, 13(3): 458-469, 2007.

Tristan. M. et al., 6-DoF haptic Rendering Using Contact Levels of Detail and Haptic Textures, 2004 Doctoral Dissertation, University of North Carolina at Chapel Hill.

Wang, Y. et al., Real-Time Interactive Simulator for Percutaneous Coronary Revascularization Procedures, Comput. Aided Surg., 3(5):211-27, 1998.

Wan et al., Quasi-Static Approximation for 6 Degrees-of-Freedom Haptic Rendering, Proceedings of the 14th IEEE Visualization 2003 (VIS'03).

* cited by examiner

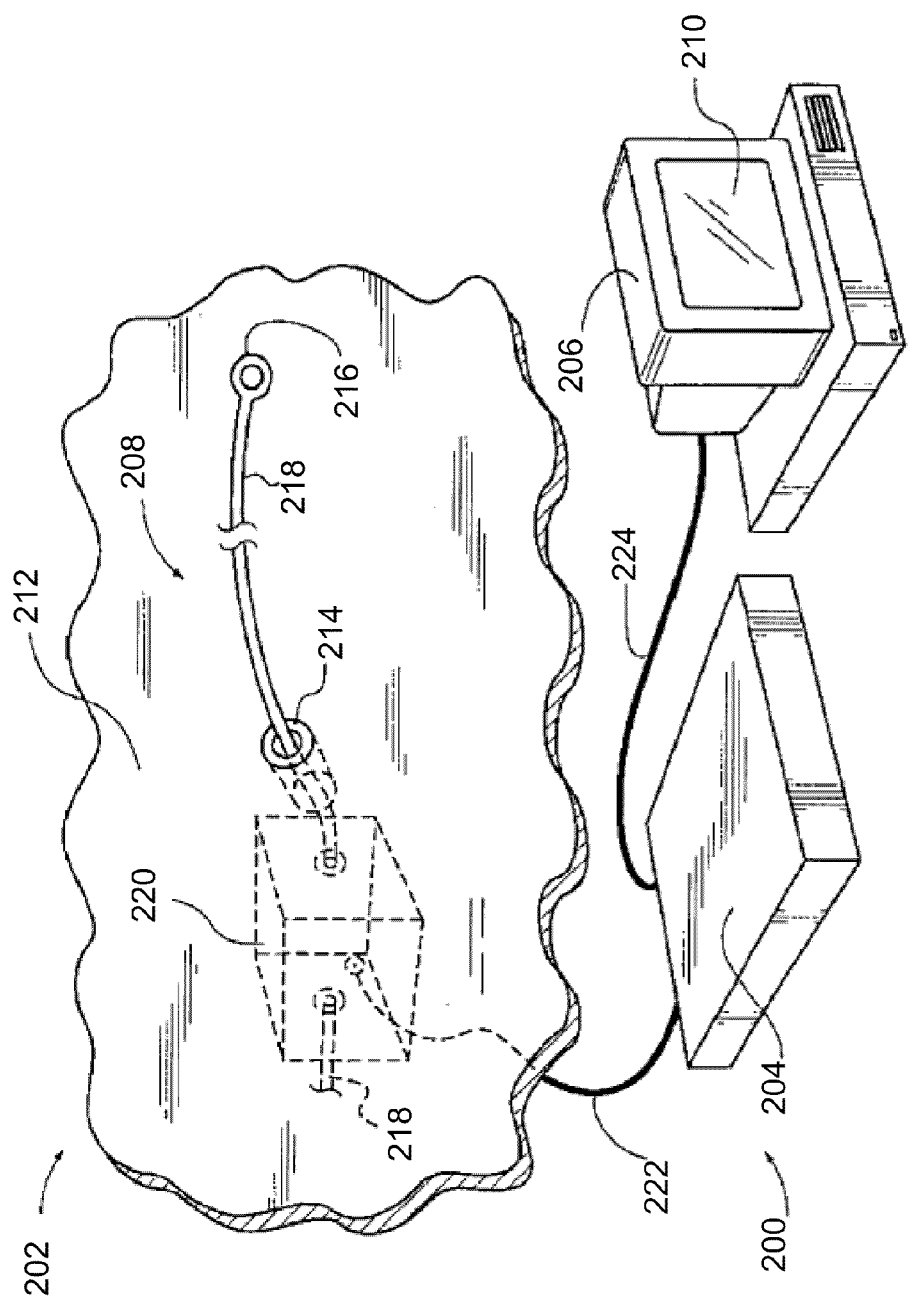

SYSTEMS AND METHODS FOR SIMULATIONS UTILIZING A VIRTUAL COUPLING

BACKGROUND

Surgical and other simulations use a computing system to model interactions between virtual objects. Typically, a simulation will use a physical object that is manipulated by a user, with the physical object represented with a corresponding virtual object in the simulation. The simulation software can be configured so that movement of the physical object corresponds to movement of the corresponding virtual object in the simulation. The real-world object may comprise an object to be handled by a user (i.e., a manipulandum) in some instances. As another example, a user's hand (or other body part) may be used to represent use of a hand or other body part in the simulation. The simulation can use physical-world movement and force applied by the physical world object as an input and provide output comprising haptic feedback using a suitable mechanism (e.g., a glove, actuators, etc.).

For example, in a surgical simulation, the physical object may represent a virtual surgical tool or the surgeon's hand during a simulated surgical procedure. As the physical object is moved, a corresponding movement of the virtual surgical tool or virtual hand can be generated in the simulation, with interaction between the virtual surgical tool and other objects modeled as part of the simulation. For example, as the manipulandum or hand is moved, a virtual surgical tool or hand may encounter different tissue or obstacles in the simulation. As the different tissue/obstacles are encountered, different amounts of pressure may be provided via actuators and/or a glove.

Unrealistic scenarios may result during the course of simulations. For example, although haptic feedback can be provided via one or more actuators when a virtual surgical tool encounters a simulated rigid obstacle (e.g., a bone), oftentimes the actuators can be overpowered by a user. Thus, an interpenetration scenario may result when the user moves the manipulandum beyond a point which it should be able to be moved, such as into a solid object.

SUMMARY

Embodiments of the present subject matter can overcome problems that may result when haptic feedback is incapable of fully controlling movement of a physical object used in the simulation. For example, embodiments of a simulation in accordance with one or more aspects of the present invention can utilize a "virtual coupling" instead of an absolute coupling between a physical object and the corresponding virtual object in the simulation. Interaction forces can be computed from the virtual coupling and provided to the user through the haptic interface. Even in the absence of an interpenetration scenario, the simulation may be less computationally intense than other methods.

Embodiments include a computing system that provides a simulation by storing values of a first plurality of nodes in memory based on tracking the position of a plurality of points of a physical object. The computing system can maintain a second plurality of nodes in memory, with each node of the second plurality of nodes corresponding to a node of the first plurality of nodes. The values of the second plurality of nodes can be used in the simulation to model interactions with other objects and to render a view of the simulated object.

During the simulation, the computing system can access data identifying a simulation boundary, such as another object in the simulated environment, movement restriction, or the like, and selectively update values of the second plurality of nodes using values of corresponding nodes of the first plurality of nodes while ensuring that the simulation boundary is not violated. Selectively updating can comprise setting at least one value of the second plurality of nodes to a value different from the value of the corresponding one of the first plurality of nodes if using the value of the corresponding node of the first plurality of nodes would violate the boundary. The first simulated object can be further defined by a set of object constraints specifying relationships between pairs of the nodes, and the object constraints can also be used in selectively updating values of the second plurality of nodes.

The computing system can determine a feedback parameter, such as a force vector, using a virtual coupling and a difference between values of one or more of the first plurality of nodes and the corresponding one(s) of the second plurality of nodes. For example, the virtual coupling may specify a force to be applied to one of the nodes when the commanded position (i.e., the value in the first plurality of nodes) differs from the value used in the simulation (i.e., the value in the second plurality of nodes) due to prevention of an interpenetration. Additionally, the values of the second plurality of nodes can be used in rendering a view of the simulated object.

These illustrative embodiments are mentioned not to limit or define the limits of the present subject matter, but to provide examples to aid understanding thereof. Additional embodiments include methods and computer readable media for providing simulations including a virtual coupling between a real and simulated tool. Illustrative embodiments are discussed in the Detailed Description, and further description is provided there. Advantages offered by various embodiments may be further understood by examining this specification and/or by practicing one or more embodiments of the claimed subject matter.

BRIEF DESCRIPTION OF THE DRAWINGS

A full and enabling disclosure is set forth more particularly in the remainder of the specification. The specification makes reference to the following appended figures.

FIG. 2 is a diagram showing another illustrative simulation system

DETAILED DESCRIPTION

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used on another embodiment to yield a still further embodiment. Thus, it is intended that this disclosure include modifications and variations as come within the scope of the appended claims and their equivalents.

Figure 1:
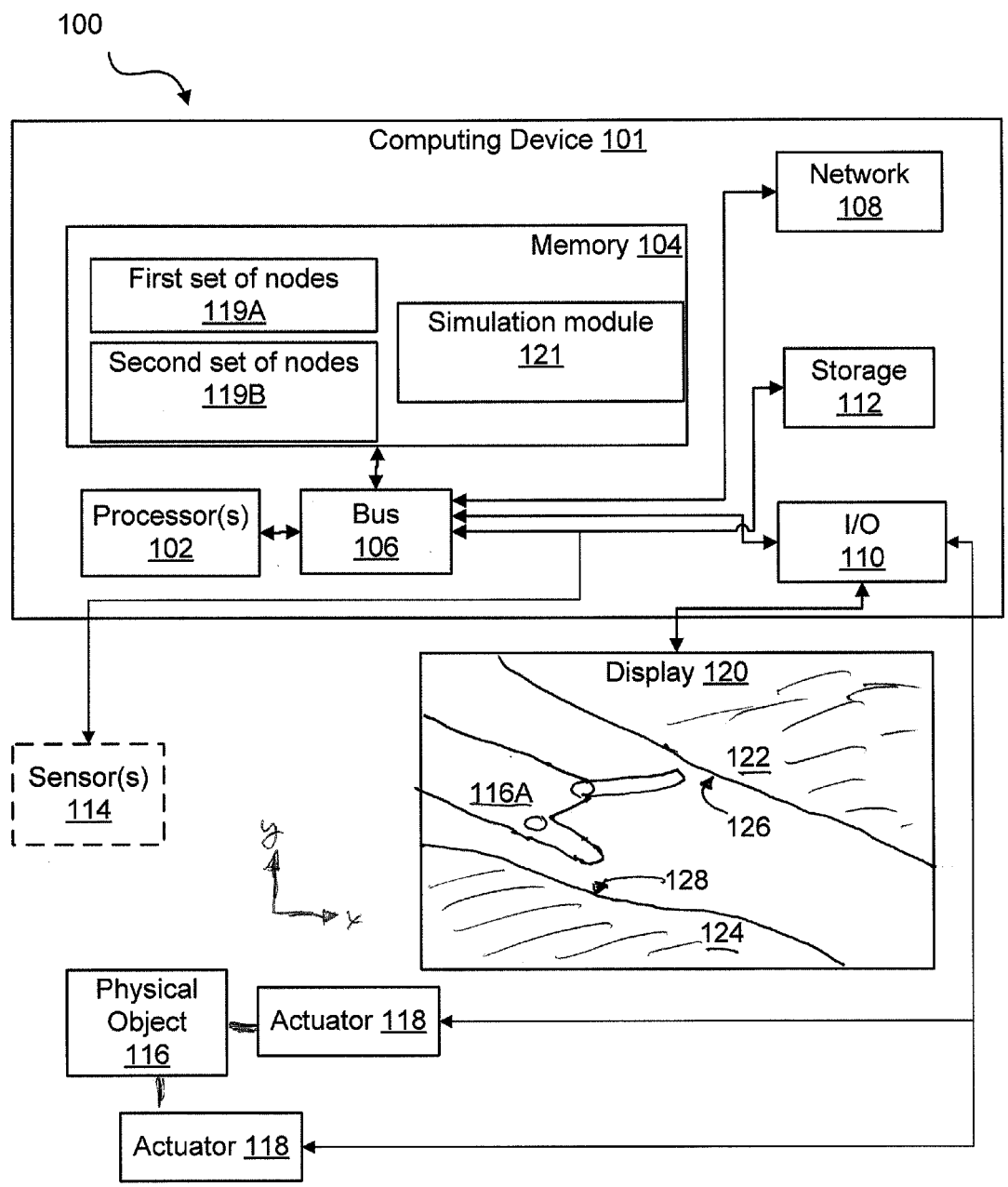
FIG. 1 is a diagram showing an illustrative simulation system

Illustrative Systems for Providing Surface-Based Haptic Effects in Conjunction with Other Haptic Effects FIG. 1 is a diagram showing an illustrative simulation system 100. In this example, the simulation system comprises a computing device 101 comprising a processor 102 connected to a memory 104 via a bus 106. Memory 104 can comprise any suitable tangible (and non-transitory) computer-readable medium such as RAM, ROM, EEPROM, or the like, embodies program components that configure operation of the computing device. In this example, computing device 101 further includes one or more network interface devices 108, input/output (I/O) interface components 110, and additional storage 112.

Network device(s) 108 can represent any components that facilitate a network connection. Examples include, but are not limited to, wired interfaces such as Ethernet, USB, IEEE 1394, and/or wireless interfaces such as IEEE 802.11, Bluetooth, or radio interfaces for accessing cellular telephone networks (e.g., transceiver/antenna for accessing a CDMA, GSM, UMTS, or other mobile communications network).

I/O components 110 may be used to facilitate connection to devices such as a one or more displays, keyboards, mice, speakers, microphones, and/or other hardware used to input data or output data. Storage 112 represents nonvolatile storage such as magnetic, optical, or other storage media included in device 101.

System 100 further includes one or more sensors 114. Sensor(s) 114 can be used to track the position of a plurality of points of a physical object 116. Physical object 116 represents one or more real-world objects that are used as a basis for modeling interactions in the course of a simulation. For example, physical object 116 may comprise a manipulandum, i.e., an object designed to be gripped or otherwise manipulated. As another example, physical object 116 may comprise an assembly that receives another object, such as a surgical tool or facsimile thereof for manipulation by a user. As a further example, physical object 116 may represent a user's hand or another body part whose motion is tracked during the course of the simulation.

Sensor(s) 114 may comprise any suitable sensing technology, and may be tailored for use with a particular physical object 116. For example, if a user's hand is used, then sensor(s) 114 may be comprised in a glove or other peripheral device worn during the simulation; the glove could also comprise actuators for force feedback. As another example, optical, magnetic, or other sensing techniques may be used to track motion of physical object 116.

In this example, simulation system 100 includes a plurality of actuators 118 configured to output haptic effects through object 116. For example, actuators may be physically coupled to physical object 116 to impart force in one or more directions. Any suitable actuator technology can be used to provide any suitable haptic effect, including a piezoelectric actuator, an electromagnetic actuator, an electroactive polymer, a shape memory alloy, a flexible composite piezo actuator (e.g. an actuator comprising a flexible material), electrostatic, and/or magnetostrictive actuators. In some embodiments, sensor(s) 114 may comprise encoders or other devices included in actuators 118.

Turning to memory 104, various program components are embodied in the memory and configure computing device 101 to provide a simulation. In this example, the program components include a plurality of nodes 119A which are updated based on tracking motion of the physical object. For example, each node may include values of an (x, y, z) coordinate in the simulation space and can be associated with a mass. Movements by the user can be identified and converted to forces applied to each of the nodes to determine updated values. A second plurality of nodes 119B are stored in memory as well; each node of the second plurality of nodes corresponds to one of the first plurality of nodes, but as will be noted below, the values are not necessarily the same.

In particular, simulation module 121 is used to selectively update values of the second plurality of nodes based on values of the corresponding nodes of the first plurality of nodes while ensuring that no simulation boundaries are violated. For instance, if no boundary is at issue, the values for the second plurality of nodes may be the same as the values of the first plurality of nodes. However, once a boundary is encountered or approached, the values of the second plurality of nodes may not follow the values of the first plurality of nodes.

Simulation module 121 can also ensuring that the resulting values of the second plurality of nodes meet a set of object constraints defining the first simulated object. For example, one embodiment defines an object in terms of four nodes and six distance constraints specifying an arrangement of the nodes. Accordingly, when one or more values for one of the second plurality of nodes are set, other values may need to be adjusted to meet the distance constraints.

Simulation module 121 may further rely on a virtual coupling that details how the simulation responds when corresponding nodes of the first and second plurality of nodes have different values, and may also include routines and methods for modeling object interactions during the course of the simulation.

Display 120 may represent a monitor, heads up display, and/or another mechanism for providing visual output. For example, in some embodiments, simulation module 121 renders a view of the first simulated object and other simulated objects as depicted in FIG. 1. Particularly, a first simulated object 116A is shown as a simulated surgical tool passing between two simulated objects 122 and 124. For example, objects 122 and 124 may represent tissue and/or bone of a simulated patient. The simulation task may comprise successfully maneuvering tool 116A without damaging the tissue/bone represented by objects 122 and 124 by providing suitable input in the x and y directions via physical object 116.

A conventional simulation technique may include data representing positions within the simulation for objects 122 and 124, with the position of object 116A determined based on movement of physical object 116. If simulated object 116A encounters wall 126 and/or 128, haptic feedback may be provided, such as feedback that would be felt if a surgical tool encountered a real wall. However, an interpenetration scenario or other unrealistic scenario may arise. For instance, a user may continue to push against actuator 118A and/or 118B despite the feedback, and may be able to move physical object 116. The corresponding representation of simulated tool 116A may pass through wall 126 and/or 128, even if such a passage would be impossible in real life.

On the other hand, embodiments of the present subject matter can avoid such scenarios by using a virtual coupling. Walls 126 and 128 may be represented in memory as a set of simulation boundaries specified in terms of permissible (or impermissible) values in the coordinate system used to define nodes 119B, which are used to represent simulated object 116A. The position of simulated object 116A can be determined based on motion of physical object 116, but if an updated value for one or more of the nodes results in a violation of one of the constraints corresponding to walls 126 and 128, the movement of physical object 116 can be ignored and/or otherwise treated differently to avoid the interpenetration scenario. A violation may result if a value of a node violates the boundary and/or if a linear combination of several nodes violates the boundary.

FIG. 2 is a perspective diagram of a system 200 for simulating coupled flexible or segmented objects in accordance with one embodiment. System 200 comprises two physical objects—a wire sliding within a catheter—during a medical procedure, but can be used to simulate any coupled segmented objects. System 200 includes a human/computer interface 202, an electronic interface 204 and a computer 206.

A catheter 208 and a wire that coaxially slides within catheter 208 are manipulated by a user and virtual reality images are displayed on a monitor 210 of computer 206 in response to such manipulations. Computer 206 can be any type of general purpose or specialized computer that includes a processor and a memory for storing instructions that are executed by the processor.

In addition to catheter 208 and wire, a human/computer interface 202 includes a barrier 212 and a "central line" 214 through which catheter 208 and wire are inserted into the "body". Barrier 212 is used to represent the portion of the skin covering the body of a patient. In one embodiment, barrier 212 is formed from a mannequin or other life-like representation of a body or body portion (e.g., the torso, arm or leg). Central line 214 is inserted into barrier 212 to provide an entry and removal point from barrier 212 for catheter 208, and to allow the manipulation of the distal portion of catheter 208 and wire within the body of the patient while minimizing tissue damage. Catheter 208 and its wire can be any commercially available catheters and wires, although in one embodiment the end of catheter 208 is removed to prevent any potential damage to persons or property since it is not required for the medical simulation. Other tools to be simulated can be coaxial to catheter 208 or otherwise coupled to catheter 208.

Catheter 208 includes a handle or "grip" 216 and a shaft 218. Grip 216 can be any conventional device used to manipulate catheter 208, or grip 216 may comprise shaft 218 itself. The wire may also include a handle so that it may be manipulated independently of catheter 208. Catheter 208 and the wire are elongated flexible objects but may be any type of objects that can be represented by connected segments.

A haptic interface 220 receives shaft 218 and the wire and applies haptic feedback on shaft 218 and wire that can be felt by the user and provides the user with a sensation that the catheter and wire are entering an actual body. In one embodiment, haptic interface 220 includes one or more actuators and other devices that generate the haptic feedback. Haptic interface 220 can be any known device for generating haptic feedback, including the haptic interface disclosed in U.S. Pat. No. 5,821,920. Haptic interface 220 also determines the position of catheter 208 and the wire within the simulated (physical) body, including whether the catheter/wire are being pushed, pulled or twisted by the user.

Electronic interface 204 receives position information from haptic interface 220 via cable 222, and transmits the information to computer 206 via cable 224. In response, computer 206 models the position of the catheter and wire and renders a graphical image of the simulation on monitor 210. Further, computer 206 generates the required haptic effects based on the position of catheter 208, and provides signals to haptic interface 220 to generate the haptic effects that are felt by the user. Particularly, a virtual catheter and/or wire can be represented in memory as a plurality of nodes. A first plurality of nodes can be maintained based on tracking motion of catheter 208 and/or the wire, and a second plurality of nodes can be updated based on values of the first plurality of nodes, a set of object constraints, and to ensure that no simulation boundaries are violated.

Additional details on simulation behavior and configuration, including modeling interactions between simulated objects, can be found in U.S. patent application Ser. Nos. 11/774,223 and 11/549,834, both of which are incorporated by reference herein in their entireties.

Simulation systems, including but not limited to those referenced above, can be configured in accordance with the present subject matter to decouple the representation of a physical object from the actual position of the object.

Figure 3A:
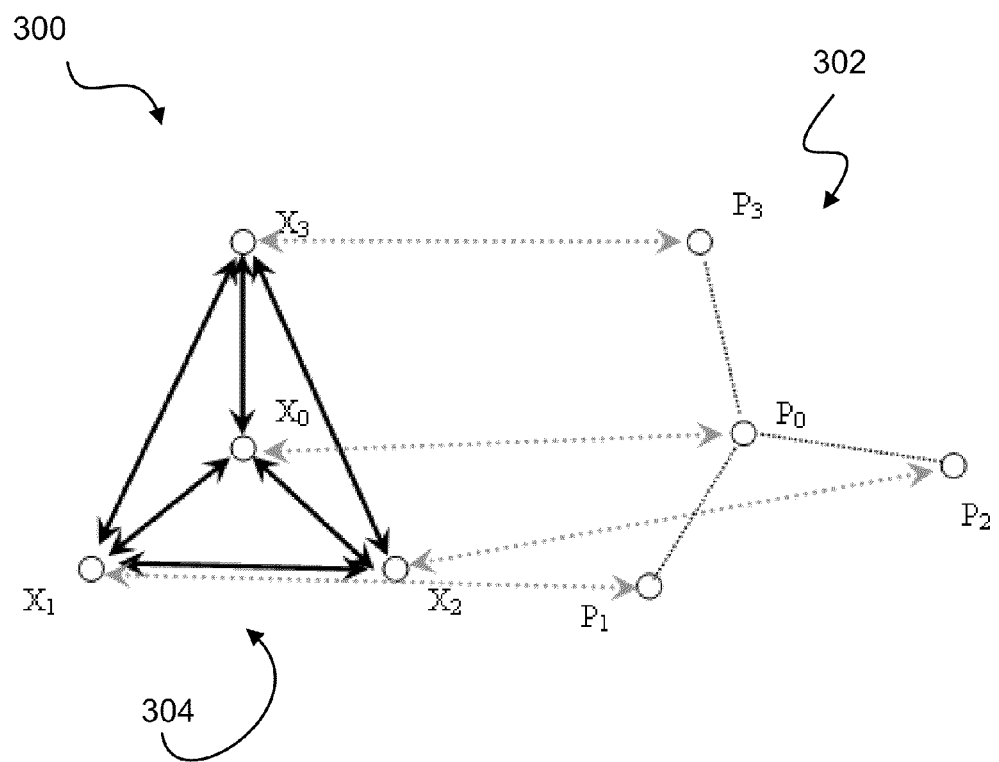
FIG. 3A is a diagram showing a mapping between a plurality of nodes defining a simulated object along with a representation of points of the corresponding physical object.

FIG. 3A is a diagram 300 showing nodes representing a physical object. Particularly, a first plurality of nodes 302 can be maintained in memory based on tracking the physical object to be represented in the simulation. A second plurality of nodes 304 can be used to represent a virtual copy of the physical object. In this example, four nodes ($X_0$ to $X_3$) are used to represent a rigid tool in a simulation. The shape of the tool is maintained through six distance constraints between the nodes (solid arrows). The nodes are individually coupled to the physical tool through a virtual coupling comprising four point attachment constraints, represented in FIG. 2 as dotted arrows to points $P_0$ to $P_3$.

As noted above, a simulation using a virtual coupling algorithm can define at least two representations of the tool, including a virtual tool represented with simulation nodes $X_0$ to $X_3$ and a representation corresponding to measured physical tool with positions $P_0$ to $P_3$ (these positions are updated from the device, e.g., via sensor(s) 114). The virtual tool separates from the physical tool when the user pulls, pushes, or otherwise moves the physical tool into configurations beyond what is possible to achieve for the simulated tool-tissue interaction system. Object constraints can be applied in setting values for the second plurality of nodes ($X_0$ to $X_3$ in this example) to ensure that the virtual tool maintains a desired shape. In this example, six distance constraints are added to the simulation to ensure that the four virtual tool nodes keep their positions relative to each other:

$C_1: \|X_0 - X_1\| = l_0$
$C_2: \|X_0 - X_2\| = l_0$
$C_3: \|X_0 - X_3\| = l_0$
$C_4: \|X_1 - X_2\| = l_0$
$C_5: \|X_1 - X_3\| = l_0$
$C_6: \|X_2 - X_3\| = l_0$

Other object constraints could be used if a non-rigid tool were to be simulated. Additionally, more or fewer than the four nodes of this example could be used in other embodiments.

The coupling between the virtual and physical tools is modeled with a virtual coupling represented here as four point attachment constraints:

$C_7: X_0 - P_0 = 0$
$C_8: X_1 - P_1 = 0$
$C_9: X_2 - P_2 = 0$
$C_{10}: X_3 - P_3 = 0$

During the simulation, values of the nodes in the second plurality of nodes (i.e. the virtual tool) can be updated based on corresponding values of the first plurality of nodes. However, if using a value of one or more of the first plurality of nodes results in a violation of a simulation boundary, the value of the corresponding node in the second plurality of nodes is set at a value that does not result in a violation of the boundary and also meets the object constraints. This is expressed generally in FIGS. 3B and 3C.

Figure 3B:
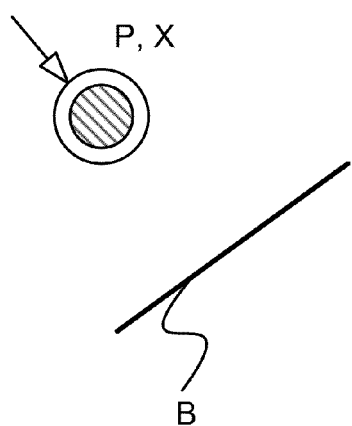
FIGS. 3B and 3C illustrate selectively updating node values based on a simulation boundary.
Figure 3C:
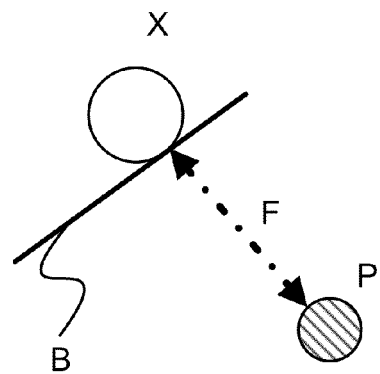

FIG. 3B shows a scenario where a node P representing the physical tool and a corresponding node X of the virtual tool have the same values. A simulation boundary B is shown to represent an object surface or other restriction on movement of the virtual tool, and as indicated by the arrow, node P and X are moving towards the boundary. As shown in FIG. 3C, the physical tool has been moved so as to command a position beyond boundary B. However, the simulation has set a value of node X in order to avoid violating the boundary. As noted below, the simulator can calculate a force F based on the coupling parameters and the difference between the values for node P and its corresponding node X.

Independent of handling interpenetration scenarios, it is has been found that the representation of the simulated object shown in FIG. 3A allows for the dynamics of the object to be expressed through the inertia of the nodes (as opposed to expressing it explicitly). The algorithm yields an optimal kinematic mapping between the physical and virtual tools through force equilibrium across all the constraints.

Contact between the simulated object and another object in the scene is modeled through point, segment, and surface constraints, where the constraint position that expresses a violation of a boundary is a function of the virtual tool nodes:

$$X = \sum_{i=0}^{3} X_i \alpha_i$$

where $\alpha_i$ are the parameters that represent how the constraint position X is expressed as a linear combination of the nodes $X_i$.

Alternatively, additional nodes can be added to the system. The following constraints express attachment of a node to the virtual tool nodes:

$$C_k : X_k - \sum_{i=0}^{3} X_i \alpha_i = 0$$

In one embodiment an additional constraint is used to express the fact that the virtual tool pivots around a fixed location Q in space:

$$C_{11}: [I-(P_1-P_0)(P_1-P_0)^T]((1-u)X_0+uX_1)$$

where I is the 3×3 identity matrix and u is a parameter that corresponds to the amount of insertion of the tool along $P_1$-$P_0$ through pivot point Q. Parameter u is updated based on the insertion of the physical device, such as a laparoscopy haptic workstation device. As an example, U.S. Pat. No. 5,623,582 discloses an apparatus used to simulate a laparoscopic medical procedure and is incorporated by reference herein in its entirety. It will be understood, however, that present embodiments can extend to any type of simulation apparatus and any type of simulated procedure.

Illustrative Methods for Simulations Utilizing Virtual Coupling

Figure 4:
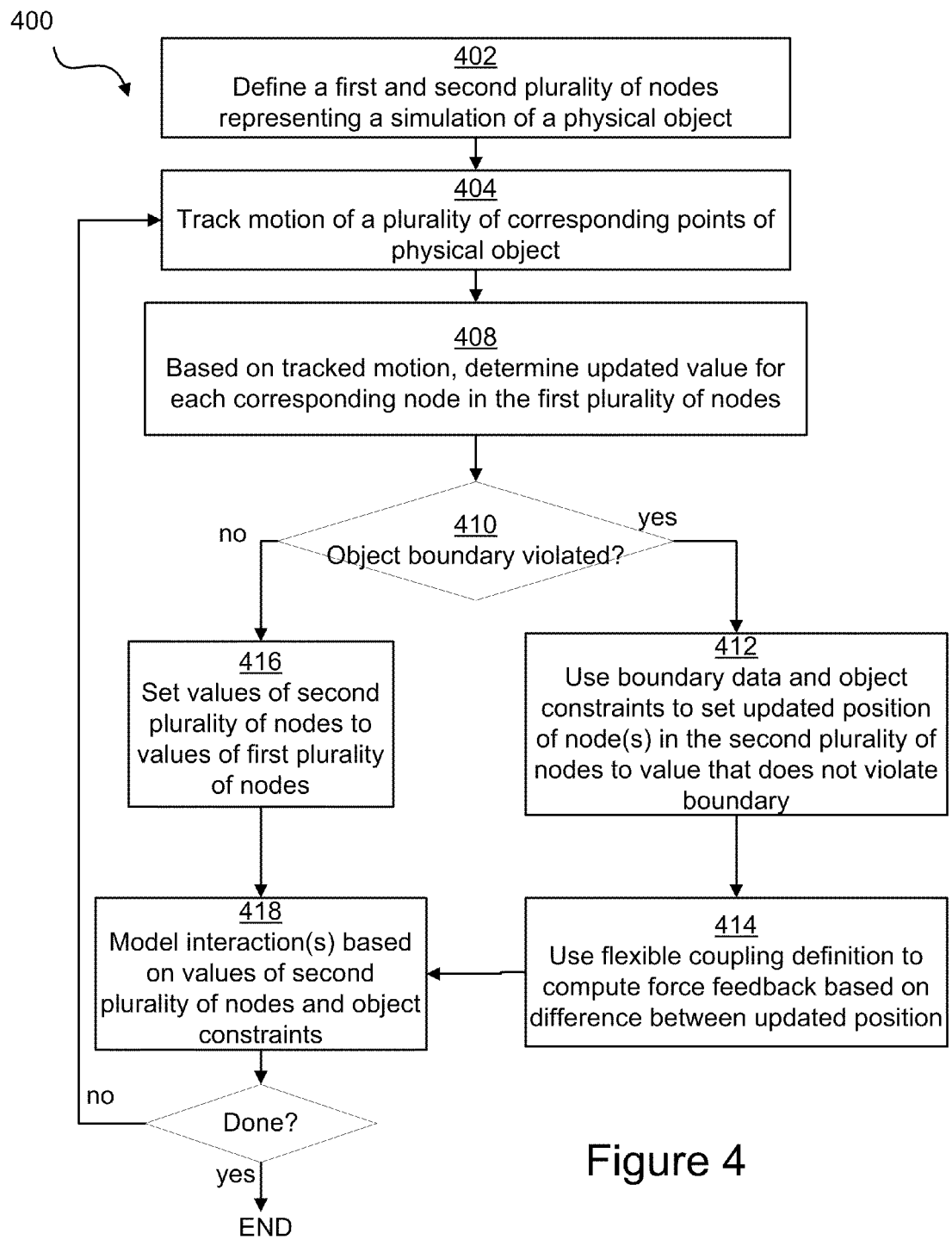
FIG. 4 is a flowchart showing an illustrative method for simulating an object using a plurality of nodes and a virtual coupling.

FIG. 4 is a flowchart showing an illustrative method 400 for simulating an object using a plurality of nodes and a virtual coupling. Block 402 represents an initialization step, namely defining a first and second plurality of nodes for use in simulating a physical object. As an example, a first set of four nodes may be defined to represent the physical object and a corresponding second set of four nodes may be defined to represent the virtual object within the simulation environment. Additionally, a set of object constraints representing the simulated object can be accessed from memory for use in the simulation. Of course, the simulation initialization can include other simulation parameters, such as simulation boundaries, other objects, etc.

Block 404 represents tracking a position of each of a plurality of points of a physical object while the physical object is moved during the simulation and storing values for a first plurality of nodes in memory, each node corresponding to one of the points. For instance, an encoder can be used to identify movement of a manipulandum or other object. The movement can be used in block 406 to determine updated values for each of the first plurality of nodes, such as (x, y, z) coordinate values in the simulated space.

Block 408 represents determining if a value of at least one of the first plurality of nodes results in a violation of a boundary defined in the simulation. For example, another simulated object (e.g., an organ or bone in a surgical simulation) may be defined in terms of simulated coordinates (e.g., a surface). The boundary may be violated if a value of the first plurality of nodes would place the node past the surface. As another example, a linear combination of a plurality of nodes may violate the boundary. If no values of the first plurality of nodes result in a violation of the boundary, the method moves to block 414, which represents setting an updated value of each of the plurality of second nodes to the value of the corresponding node of the first plurality of nodes.

However, if a value of at least one of the first plurality of nodes results in a violation of the boundary, the method proceeds to block 410. Block 410 represents setting an updated value for one or more of the second plurality of nodes so that the values of the second plurality of nodes do not result in a violation of the boundary but also meet the set of object constraints. For example, the object constraints may represent distance constraints between pairs of the second plurality of nodes to ensure realistic behavior—for instance, if one node (e.g., one end of a tool) is set to a position outside a boundary, then the distance constraints can ensure the other nodes (e.g., other end of the tool) are also moved appropriately.

Block 412 represents accessing a virtual coupling between the first and second plurality of nodes and using the difference between the values of the first plurality of nodes (i.e., the physical object) and the second plurality of nodes (i.e., the virtual object) to determine a feedback parameter. For example, the feedback parameter may comprise a force feedback parameter that indicates one or more types of haptic feedback to provide. This may, for instance, allow for the physical object to "push back" while a user attempts to interpenetrate an object. As another example, the feedback parameter may comprise data used to provide visual feedback.

Block 416 is reached in either branch, and represents modeling interactions, as appropriate, based on the values of the second plurality of nodes and object constraints. For example, the values of the second plurality of nodes can be used to render a view of the simulated object. Accordingly, even if the values of the first plurality of nodes would lead to an unrealistic scenario, the second plurality of nodes respect the simulation boundaries and allow for a realistic rendering. The tool can be rendered using a visual skin, lighting effects, etc. based on the second plurality of nodes (along with other simulated objects) as will be apparent to one of skill in the art.

As another example, the values of the second plurality of nodes can be used as inputs to techniques for simulating interaction of rigid and/or flexible bodies. This may include providing a haptic effect through the physical object based on at the modeled interaction. Block 418 represents checking whether the simulation is terminated and, if not, returning to block 404.

Figure 5:
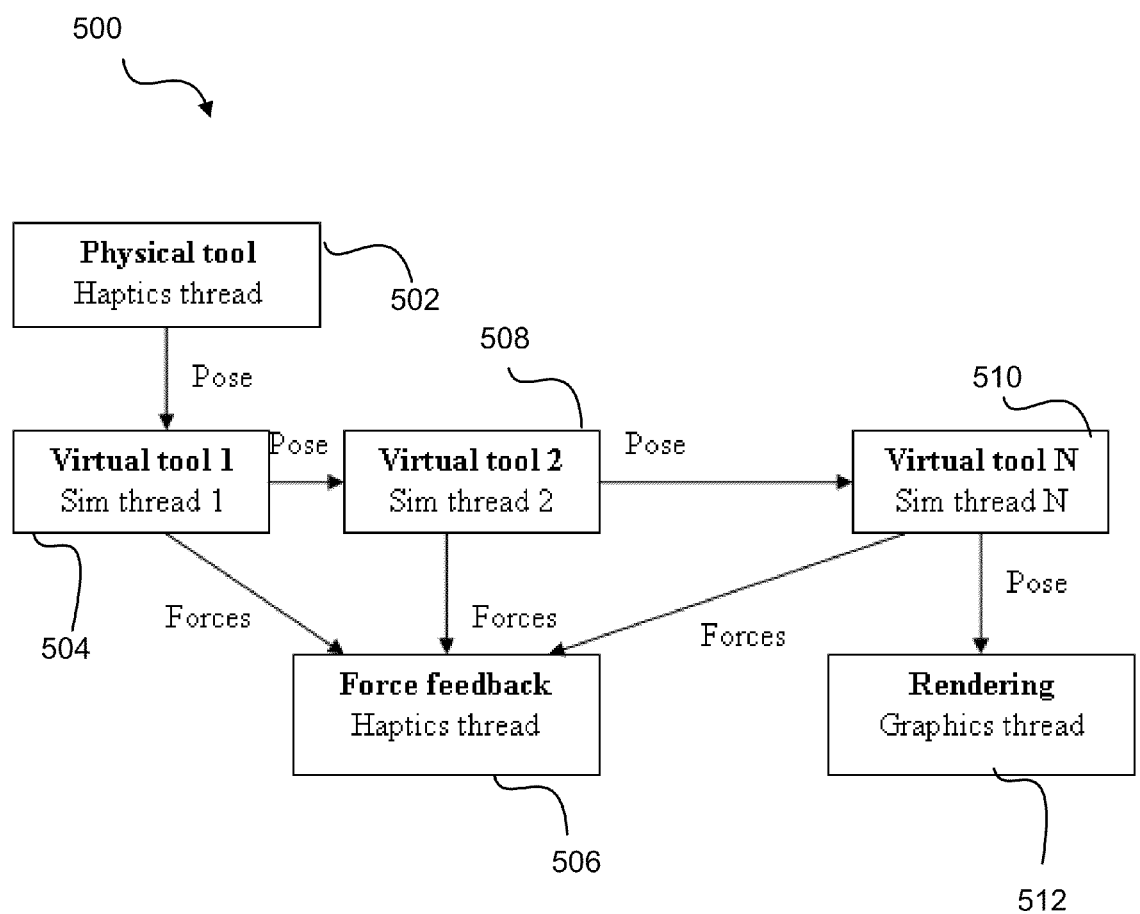
FIG. 5 is a data flow diagram showing use of multiple execution threads for carrying out a simulation featuring multiple simulated tools.

In some embodiments, simulation tasks can be carried out using different processor threads on the same processor or even on different processors. FIG. 5 is a data flow diagram illustrating one such embodiment. In this example, a physical tool is manipulated by a user and generates a position update to the first plurality of nodes (labeled as "pose" in FIG. 5) as shown at 502. This position data is used as shown at 504 to update values of one or more of a second plurality of nodes representing a virtual representation of the tool in a first processor thread. The updated node values are used as shown at 506 to determine a feedback parameter, such as a force feedback parameter to be applied using one or more actuators (e.g., embedded in or coupled to the tool). For instance, as noted above, if the physical and virtual representations differ, a force feedback can be calculated using the virtual coupling.

In this example, representations of the virtual tool are chained together. For instance, another representation of the same tool ("Virtual tool 2") is running in a second execution thread as shown at 508. "Virtual tool 2" can be represented in thread 508 by a third plurality of nodes, along with the object constraints. Updated values for one or more of the second plurality of nodes can be used as representing 'movement' of the first virtual tool and can be checked against a second simulation boundary. If the second simulation boundary would be violated, then values of the third plurality of nodes may differ from the corresponding values of the second plurality of nodes. Interactions between the virtual tool as represented in 508 and/or any differences between the second and third plurality of nodes can be used to determine an additional feedback parameter for use by the haptics thread shown at 506.

The chaining of virtual tools can be extended to any number of virtual tools as indicated at block 510 ("Virtual tool N"). In this example, the updated nodes for virtual tool N are used by a graphics thread 512 in determining how to render the simulation scene.

Figure 6:
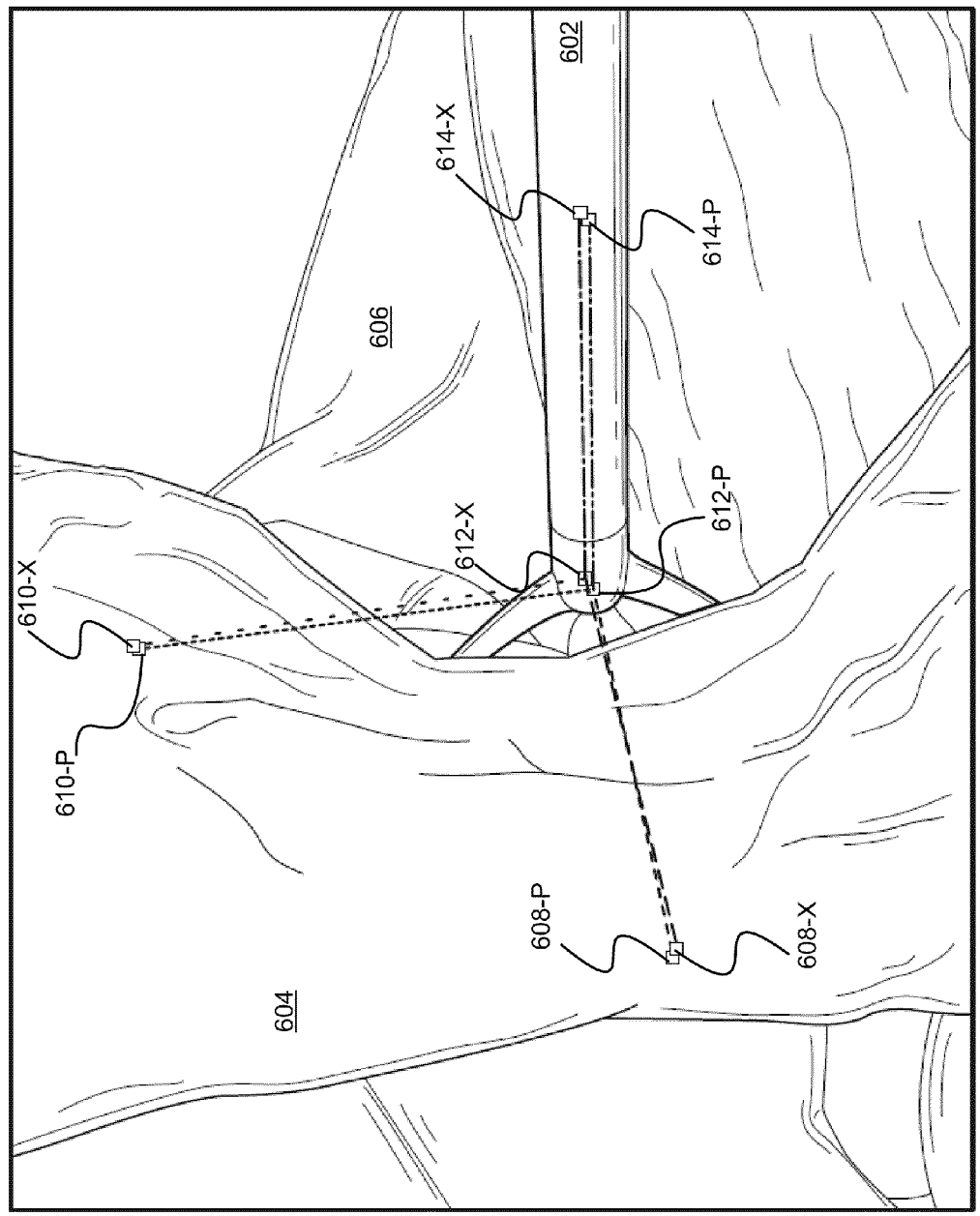
FIGS. 6 and 7A-7B show illustrative displays that can be rendered during a simulation.

FIG. 6 shows an example of a simulation scene as rendered, along with illustrations of the first and second plurality of points representing a virtual tool. In this example, a virtual laparoscopic tool 602 has encountered a first simulated object 604 (e.g., an adhesion). Background 606 depicts other components of the simulation scene, such as a liver and gall bladder. In this example, a first plurality of nodes 608-P, 610-P, 612-P, and 614-P are shown, with the node values are set based on the movement/position of a physical object.

A second plurality of nodes 608-X, 610-X, 612-X, and 614X are also shown, and are the basis for rendering the view of tool 602. The values of nodes 608-X, 610-X, 612-X, and 614-X can be set based on values of nodes 608-P through 614-P and simulation boundaries (such as surfaces of object 604). In this example, there is a slight interpenetration between the tips of the scissors of tool 602 and the deforming adhesion 604. Thus, a slight difference in the position of the first and second plurality of nodes is shown. It will be understood that, in practice, the actual nodes may not be included in the simulation rendering. If no interpenetration was occurring (and no other simulation boundaries would be violated), the node values could be the same.

In the example of FIG. 6, background 606 depicted images of the simulation environment, such as a liver and gallbladder. In some embodiments, either or both the liver and gallbladder could also comprise simulated objects which could be interacted with during the simulation.

As noted above, in some embodiments multiple representations of a tool can be used to divide simulation across multiple processor threads. For example, a first thread may access values for nodes 608-P, 610-P, 612-P, and 614-P and set values for nodes 608-X, 610-X, 612-X, and 614-X based on one or more boundaries associated with object 604 (and the object constraints defining the tool). A second thread may access the values for nodes 608-X, 610-X, 612-X, and 614-X as set by the first thread and set values for a third plurality of nodes based on boundaries associated with another object and its constraints, such as boundaries and/or constraints associated with a simulated liver. The third plurality of nodes could be used to render the view of the tool. Accordingly, a simulation can account for multiple objects while using relatively simpler (and faster) calculations than would otherwise be required. If more object interactions were desired, then a fourth plurality of nodes could be updated based on the values of the third plurality of nodes and boundaries associated with an additional object, and so on. To the extent each thread generates feedback parameters, the various feedback parameters can be summed for presentation to a user (e.g., as a sum of force vectors) via one or more haptic effects.

Figure 7A:
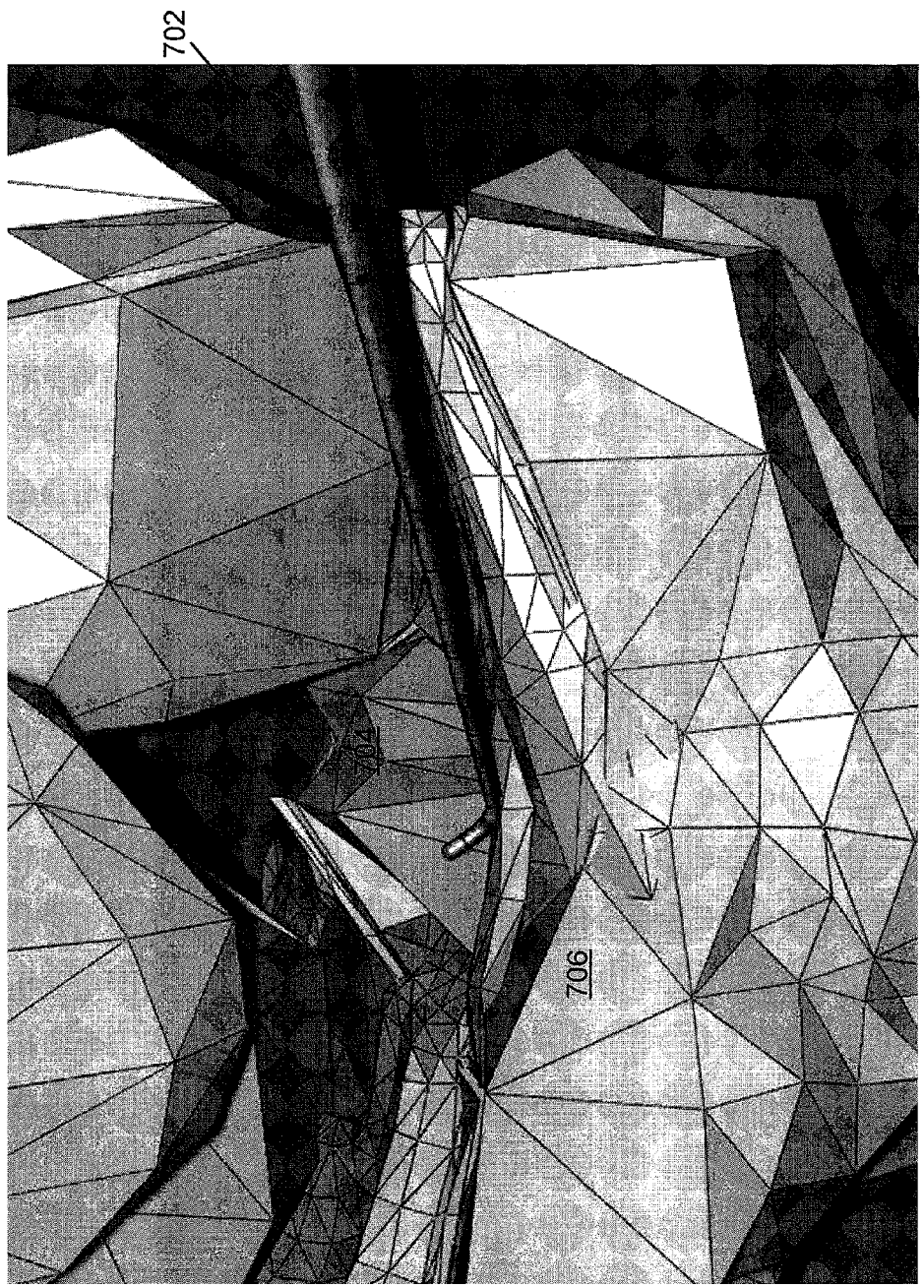
Figure 7B:
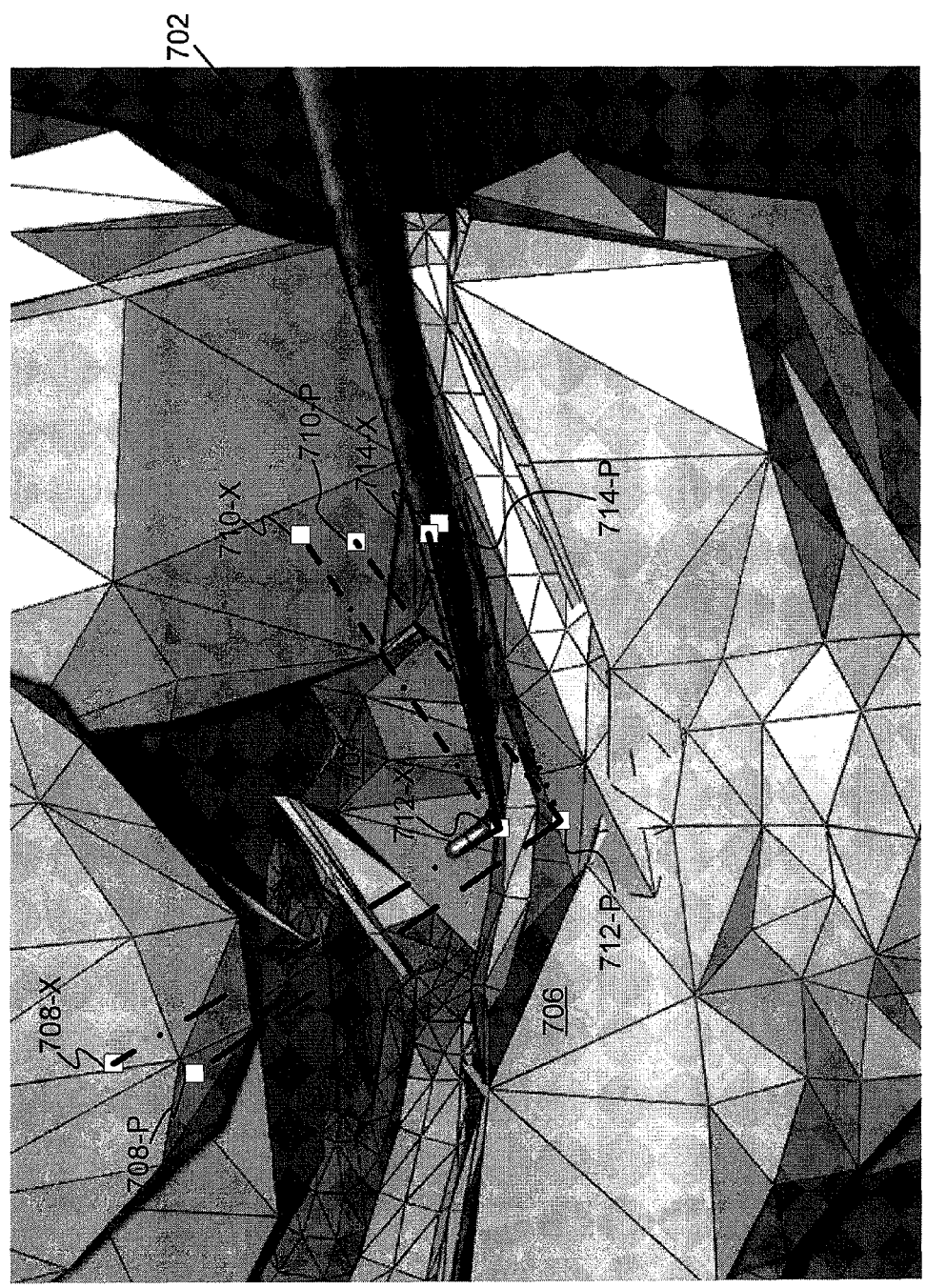

FIG. 7A shows an example of another rendering of a simulated environment. In this example, a tool 702 is encountering bones 704 and 706. FIG. 7B illustrates the tool as represented by a first and second plurality of nodes. In particular, the user has moved a physical object into a position/orientation that, if used directly, would cause the simulated tool to violate one or more simulation boundaries and interpenetrate object 706. This can be seen especially at node 712-P of the first plurality of nodes, which also includes nodes 708-P, 710-P, and 714-P. Accordingly, the second plurality of nodes 708-X, 710-X, 712-X, and 714-X have separated. For instance, values of node 712-X have been set at the boundary defining bones 704/706. Due to the distance constraints, nodes 708-X, 710-X, and 714-X have also been set at values that differ from the corresponding values of nodes 708-P, 710-P, and 714-P. Additionally, if the simulator employs force feedback, an appropriate feedback value may be generated based on the differences in values, particularly the differences in values between 712-P and 712-X. For example, the force feedback may be tailored to provide a sensation of node 712-P attempting to return to match the value of node 712-X. In some embodiments, the virtual coupling is defined in terms of a spring constant so that the force feedback results in such a sensation based on the distance and direction between a node of the first plurality of nodes and the corresponding node of the second plurality of nodes.

In practice, and depending on how the objects and other portions of the simulated environment are rendered and defined, some slight interpenetration may result. Thus, the examples above are not intended to exclude the possibility of interpenetration in a simulation rendering.

General Considerations

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. A computer-implemented simulation method, comprising:
    tracking a position of each of a plurality of points of a physical object while the physical object is moved and storing values for a first plurality of nodes in memory, each node corresponding to one of the points;
    defining a second plurality of nodes in memory, the values of the second plurality of nodes and a set of object constraints representing a simulated object corresponding to the physical object; and
    determining if a value of at least one of the first plurality of nodes results in a violation of a boundary defined in the simulation; and
    if a value of at least one of the first plurality of nodes results in a violation of the boundary:
        setting an updated value for one or more of the second plurality of nodes so that the values of the second plurality of nodes do not result in a violation of the boundary and meet the set of object constraints,
        accessing a virtual coupling between the first and second plurality of nodes, and
        determining a force feedback parameter using the virtual coupling and a difference in a value between at least one of the first plurality of nodes and the value of the corresponding one of the second plurality of nodes;
    if no values of the first plurality of nodes violate the boundary:
        setting an updated value of each of the plurality of second nodes to the value of the corresponding node of the first plurality of nodes.

2. The computer-implemented method set forth in claim 1, further comprising:
    rendering a view of the simulated object based on the values of the second plurality of nodes.

3. The computer-implemented method set forth in claim 1, further comprising:
    providing a haptic effect through the physical object based on the force feedback, the haptic effect provided using at least one actuator.

4. The computer-implemented method set forth in claim 1, further comprising:
    modeling an interaction between the simulated object and a second simulated object based on the values of the second plurality of nodes; and
    providing a haptic effect through the physical object based on at the modeled interaction, the haptic effect provided using at least one actuator.

5. The method set forth in claim 1, wherein the second plurality of nodes comprises four nodes and the set of object constraints comprises six distance constraints, each distance constraint defining a distance between a pair of the second plurality of nodes.

6. The method set forth in claim 1,
    wherein the simulation boundary corresponds to a boundary of a second simulated object,
    wherein defining a second plurality of nodes in memory and determining if a value of at least one of the first plurality of nodes results in a violation of a simulation boundary are carried out in a first processor thread configured to provide the values of the second plurality of nodes to a second processor thread, and
    wherein the method further comprises:
    in the second processor thread:
    defining a third plurality of nodes in memory, the values of the third plurality of nodes representing a copy of the simulated object;
    determining if a value of at least one of the second plurality of nodes results in a violation of a boundary of a third simulated object; and
    if the value of at least one of the nodes results in a violation of the boundary of the third simulated object:
        setting an updated value of one of the third plurality of nodes to a value that does not results in a violation of the boundary,
        setting an updated value of one or more others of the third plurality of nodes based on the set of object constraints,
        accessing the virtual coupling, and
        determining an additional force feedback parameter using the virtual coupling and a difference in a value between at least one of the second plurality of nodes and the value of the corresponding one of the third plurality of nodes; and
        rendering a simulation view based on the values of the third plurality of nodes.

7. The method set forth in claim 6, further comprising:
providing a haptic effect through the physical object based on the force feedback parameters determined by the first and second processor threads.

8. A simulation system, comprising:
a sensor and a computing device, the computing device comprising a processor and a memory, the memory embodying program components that configure the computing device to:
use the sensor to track a position of a plurality of points of a physical object;
store values for each of a first plurality of nodes in the memory based on the tracked position of the points;
define a second plurality of nodes in memory, the values of the second plurality of nodes and a set of object constraints representing a simulated object corresponding to the physical object, each one of the second plurality of nodes corresponding to one of the first plurality of nodes;
determine if a value of at least one of the first plurality of nodes results in a violation of a boundary defined in the simulation;
if the value of at least one of the first plurality of nodes results in a violation of the boundary:
set an updated value for one or more of the second plurality of nodes so that the values of the second plurality of nodes do not violate the boundary and meet the set of object constraints,
access a virtual coupling between the first and second plurality of nodes, and
determine a feedback parameter based on the virtual coupling and a difference between a value in the second plurality of nodes and a corresponding value in the first plurality of nodes;
if no values of the first plurality of nodes violate the boundary:
set an updated value of each of the plurality of second nodes to the value of the corresponding node of the first plurality of nodes.

9. The simulation system set forth in claim 8, wherein the computing device is further configured to render view of the simulated object based on the values of the second plurality of nodes.

10. The simulation system set forth in claim 8, further comprising:
a manipulandum, wherein the manipulandum is the physical object.

11. The simulation system set forth in claim 10, further comprising:
an actuator coupled to the manipulandum,
wherein the feedback parameter is a force feedback parameter, and
wherein the computing device is further configured to provide a signal to the actuator to provide a haptic effect based on the force feedback parameter.

12. The simulation system set forth in claim 11, wherein the computing device is further configured to:
model an interaction between the simulated object and a second simulated object based on the values of the second plurality of nodes; and
provide a signal to the actuator to provide a haptic effect based on the modeled interaction.

13. The simulation system set forth in claim 8,
wherein the simulation boundary corresponds to a boundary of a second simulated object,
wherein defining a second plurality of nodes in memory and determining if a value of at least one of the first plurality of nodes results in a violation of a simulation boundary are carried out in a first processor thread, and
wherein the computing device is further configured to utilize a second processor thread to:
determine the values of the second plurality of nodes as set by the first processor thread;
define a third plurality of nodes in memory, the values of the third plurality of nodes representing a copy of the simulated object;
determine if a value of at least one of the second plurality of nodes results in a violation of a boundary of a third simulated object; and
if the value of at least one of the nodes results in a violation of the boundary of the third simulated object:
set an updated value for one or more of the third plurality of nodes so that the values of the third plurality of nodes do not violate the boundary of the third simulated object and meet the set of object constraints,
access the virtual coupling, and
determine an additional feedback parameter based on the virtual coupling and a difference between a value in the third plurality of nodes and a corresponding value in the second plurality of nodes;
if no values of the first plurality of nodes violate the boundary:
set an updated value of each of the third plurality of nodes to the value of the respective node of the first plurality of nodes.

14. The simulation system set forth in claim 13, wherein the computing device comprises a first and second processor, the first processor thread is executed by the first processor, and the second processor thread is executed by the second processor.

15. The simulation system set forth in claim 13,
wherein the feedback parameters each comprise a force feedback parameter and the system further comprises an actuator coupled to a manipulandum,
wherein the computing device is further configured to provide a signal to the actuator to provide a haptic effect based on the force feedback parameters.

16. A non-transitory computer storage medium embodying program code executable by a computing system, the program code comprising:
program code that configures the computing system to access data representing a position of a plurality of points of a physical object;
program code that configures the computing system to store values of a first plurality of nodes in memory based on tracking the position of the plurality of points;
program code that configures the computing system to access data identifying a simulation boundary;
program code that configures the computing system to selectively update values of a second plurality of nodes using values of corresponding nodes of the first plurality of nodes while ensuring that the simulation boundary is not violated, wherein selectively updating comprises setting at least one value of the second plurality of nodes to a value different from the value of the corresponding one of the first plurality of nodes if the value of the corresponding node of the first plurality of nodes results in a violation of the boundary;
program code that configures the computing system to determine a feedback parameter using a virtual coupling if a value of the second plurality of nodes differs from the corresponding value of a node of the first plurality of nodes; and program code that configures the computing system to provide simulation output based on the feedback parameter.

17. The computer storage medium set forth in claim 16, wherein selectively updating further comprises using a set of object constraints when setting values of the second plurality of nodes.

18. The computer storage medium set forth in claim 16, further comprising:
  program code that configures the computing system to selectively update values of a third plurality of nodes using values of corresponding nodes of the second plurality of nodes as updated while ensuring that a second simulation boundary is not violated, wherein selectively updating values of the third plurality of nodes comprises setting at least one value of the third plurality of nodes to a value different from the value of the corresponding one of the second plurality of nodes if the value of the corresponding node of the second plurality of nodes results in a violation of the second simulation boundary; and
  program code that configures the computing system to provide simulation output based on the values of the third plurality of nodes.

19. The computer storage medium set forth in claim 18, wherein the program code that configures the computing system to selectively update values of the third plurality of nodes configures the computing system to utilize a processor thread different from a processor thread used to selectively update values of the second plurality of nodes.

\* \* \* \* \*

UNITED STATES PATENT AND TRADEMARK OFFICE
CERTIFICATE OF CORRECTION

PATENT NO. : 8,442,806 B2
APPLICATION NO. : 12/716903
DATED : May 14, 2013
INVENTOR(S) : Milan Ikits et al.

It is certified that error appears in the above-identified patent and that said Letters Patent is hereby corrected as shown below:

In the Specification

Column 6, Lines 44 through 49, please replace -

$$C_1 : \| X_0 - X_1 \| = l_0$$
$$C_2 : \| X_0 - X_2 \| = l_0$$
$$C_3 : \| X_0 - X_3 \| = l_0$$
$$C_4 : \| X_1 - X_2 \| = l_0$$
$$C_5 : \| X_1 - X_3 \| = l_0$$
$$C_6 : \| X_2 - X_3 \| = l_0$$

with $$C_1 : \| X_0 - X_1 \| = l_0$$
$$C_2 : \| X_0 - X_2 \| = l_0$$
$$C_3 : \| X_0 - X_3 \| = l_0$$
$$C_4 : \| X_1 - X_2 \| = l_0 \sqrt{2}$$
$$C_5 : \| X_1 - X_3 \| = l_0 \sqrt{2}$$
$$C_6 : \| X_2 - X_3 \| = l_0 \sqrt{2}$$

Signed and Sealed this
Twentieth Day of August, 2013

Teresa Stanek Rea
*Acting Director of the United States Patent and Trademark Office*